United States Patent [19]
King et al.

[11] Patent Number: 4,956,177
[45] Date of Patent: Sep. 11, 1990

[54] METHOD FOR INHIBITING FUNGI

[75] Inventors: Stephen W. King, Sarasota, Fla.; Geoff G. Fowler, Crewkerne, United Kingdom; Peter A. Vandenbergh, Sarasota, Fla.

[73] Assignee: Microlife Technics, Inc., Sarasota, Fla.

[21] Appl. No.: 794,468

[22] Filed: Nov. 4, 1985

[51] Int. Cl.$^5$ .................. A01N 63/00; C12P 1/04; C12N 1/20; A21D 2/00
[52] U.S. Cl. ............................ 424/93; 435/170; 435/856; 435/252.9; 426/9; 426/41; 426/61
[58] Field of Search ............... 435/253, 170, 856, 853, 435/854, 855, 252.9; 426/9, 41, 61; 424/93

[56] References Cited
U.S. PATENT DOCUMENTS
4,579,740  4/1986  Matrozza ........................... 435/856

OTHER PUBLICATIONS

Goering, H. K., et al., USDA Publication 387–398 (1970).
Tilley, J. M. A., et al., J. Brit. Grassl. Soc. 18:104 (1963).
Kjeldahl, AOAC; 12th Edition (1975).

Primary Examiner—Elizabeth C. Weimar
Assistant Examiner—Irene Marx
Attorney, Agent, or Firm—Ian C. McLeod

[57] ABSTRACT

A method for providing fungal inhibition using *Lactobacillus casei* var. rhamnosus which produces an antifungal substance is described. Bacterial compositions of LCR are also described. The method and compositions are particularly useful for producing fermented foods.

5 Claims, No Drawings

METHOD FOR INHIBITING FUNGI

BACKGROUND OF THE INVENTION (1) Field of the Invention

The present invention relates to a method and composition using or containing a Lactobacillus having the identification characteristics of *Lactobacillus casei* var. *rhamnosus* NRRL-B-15972 and having antifungal properties. In particular the present invention relates to the use of the Lactobacillus in foods.

(2) Prior Art

The use of lactic acid producing bacteria in methods for producing fermented foods is well known to those skilled in the art. Thus for instance fermented meats (e.g. sausages) and vegetables (e.g. pickles) are all produced using these methods. Members of the genus Lactobacillus have been used extensively for this purpose.

It is believed strains of Lactobacillus which produce fungal inhibiting substances are unknown to those skilled in the art. Thus a strain which produces an antifungal substance would be very useful in foods and also in or on other materials, such as living plants, where fungi are a problem.

OBJECTS

It is therefore an object of the present invention to provide compositions including a Lactobacillus which produces antifungal substances. Further it is an object of the present invention to provide a method which uses this Lactobacillus for mold inhibition. These and other objects will become increasingly apparent by reference to the following description.

GENERAL DESCRIPTION

The present invention relates to a method of treating a material which comprises incorporating in or on the material living cells of a *Lactobacillus casei* having the essential identification characteristics of *Lactobacillus casei* var. *rhamnosus* NRRL-B-15972 which produces an antifungal substance. Further the present invention relates to a storage stable biologically pure culture of a *Lactobacillus casei* having the essential identification characteristics of *Lactobacillus casei* var. *rhamnosus* NRRL-B-15972 which produces a fungal inhibiting substance.

Essentially any material can be treated with the antifungal *Lactobacillus casei* var. *rhamnosus* NRRL-B-15972. It is preferred that the material be a food and that the food be fermented, since the antifungal *Lactobacillus casei* var. *rhamnosus* NRRL-B-15972 of the present invention generates lactic acid in situ from glucose and other sugars present or introduced into the foods. The present strain is particularly useful where the fermented food is prone to microbial spoilage such as is encountered with silage. Plants can be treated with this Lactobacillus to prevent fungal infection. Other materials such as plastics or rubber can be protected by combining the cells with these materials.

The material or food should contain at least about $10^5$ cells per gram. Preferably the range is between about $10^6$ and $10^9$ cells per gram. The antifungal substance is cell associated, so a sufficient population is needed to prevent fungal growth.

The antifungal *Lactobacillus casei* var. *rhamnosus* can be stored in frozen or lyophilized form as is well known to those skilled in the art. The frozen form is preferred using freezing stabilizing agents such as glycerol or xanthan gum because lyophilization causes some die-off of the bacteria. The concentrates normally contain between about $10^{10}$ and $10^{12}$ cells per gm.

Plasmids and genetic material in the antifungal *Lactobacillus casei* var. *rhamnosus* NRRL-B-15972 can be transferred to other species of Lactobacillus. Any Lactobacillus having the essential antifungal characteristics of the strain NRRL-B-15972 is included within the scope of the present invention.

SPECIFIC DESCRIPTION

*Lactobacillus casei* var. *rhamnosus* NRRL-B-19572 has the following characteristics set forth in Table I:

TABLE I (1) Characterization:

| | | |
|---|---|---|
| Morphology | − | rods (typical of isolate: |
| Gram rx | + | motility - |
| Catalase | − | |
| mannitol | + | |
| mannose | + | |
| melibiose | − | |
| raffinose | − | |
| galactose | ± | |
| sorbitol | + | |
| sucrose | + | |
| adonitol | ± | |
| arabinose | + | |
| cellobiose | + | |
| glucose | + | |
| dulcitol | − | |
| salicin | + | |
| glycerol | − | |
| inositol | ± | |
| lactose | + | |
| maltose | + | |
| xylose | − | |
| trehalose | + | |
| esculin | + | |
| fructose | + | |
| rhamnose | + | |
| starch | − | |
| nitrate reductase | − | |
| ONPG | − | |

(2) Heavy growth in MRS broth (Difco, Detroit, Michigan) at a wide range of temperatures.

(3) Inhibits the following fungi on MRS agar and Potato Dextrose agar supplemented with 1% Bacto-Peptone (PDAP) - (all media by Difco, Detroit, Michigan):

| | MRS | PDAP |
|---|---|---|
| *P. oxalicum* | + | ± |
| *Geotricum candidum* | − | − |
| *Schlerotinia schlerotiorum* | + | + |
| *Botrytis cinereo* | + | + |
| *Verticillium sp.* | + | − |
| *Fusarium solani* | + | + |
| *Monilina fructicola* | + | + |
| *Aspergillus fumigatus* | + | − |
| *Aspergillus flavus* | + | ± |
| *Aspergillus terreus* | + | ± |

(4) *L. casei* var. *rhamnosus* NRRL-B-15972 grew in a defined medium (Folic Acid Assay Medium - Difco) and inhibited the above mentioned molds. Nutritional studies showed that yeast extract or molasses at 1% wt/v, added to the defined medium stimulated growth of NRRL-B-15972 and appeared to enhance the fungal inhibitory property of the bacteria.

EXAMPLE I

It was found that *Lactobacillus casei* var. *rhamnosus* NRRL-B-19572 could be frozen without problem and with virtually no die-off of cells. The frozen cells had a long shelf life (6 months) with little die-off. The lyophilization characteristics of *Lactobacillus casei* var. *rham-* nosus NRRL-B-19572 with different additives was also studies.

(1) *Lactobacillus casei* var. *rhamnosus* NRRL-B-15972 was grown overnight at 35° C. in MRS (Difco, Detroit, Mich.) broth (1000 mL), centrifuged and resuspended in 90 mL of spent medium (10 times culture).

(2) Eleven mL of 10X culture was introduced into lyophilization bottle and the pH adjusted to 5.8 with NaOH.

(3) The following additives each were added to the bottles:

| | |
|---|---|
| 2% monosodium glutamate (MSG) | 0.22 g |
| 1% monosodium glutamate (MSG) | 0.4 g |
| 2% non-fat dry milk (NFDM) | 0.22 g |
| 1% non-fat dry milk (NFDM) | 0.11 g |
| 2% maltodextrin (MD) | 0.22 g |
| 1% maltodextrin (MD) | 0.11 g |
| Control = no additives | |

The 10X culture was mixed with each lyophilized 6 hours after freezing in a dry ice and methanol bath. Viable counts were taken on the cells before and after concentration and after lyophilization.

The results were as follows:
Overnight culture = $3.1 \times 10^9$ CFU
10X culture — $2.5 \times 10^{10}$ CFU Lyophilized Cultures

| | | |
|---|---|---|
| Control | = $1.37 \times 10^{10}$% die off* | = 43.2 |
| 2% MSG | = $1.54 \times 10^{10}$% die off | = 38.4 |
| 1% MSG | = $1.41 \times 10^{10}$% die off | = 43.6 |
| 2% NFDM | = $1.31 \times 10^{10}$% die off | = 47.6 |
| 1% NFDM | = $1.93 \times 10^{10}$% die off | = 30.8 |
| 2% MD | = $1.34 \times 10^{10}$% die off | = 46.4 |
| 1% MD | = $1.19 \times 10^{10}$% die off | = 52.4 |

*Based upon 10X culture

The best results here were obtained by using 2% MSG and 1% NFDM, respectively. Maltodextrin was no better than the control. Either 2% MSG or NFDM is suitable for lyophilization; however, other well known lyophilization agents can be used.

EXAMPLE II

The effect *Lactobacillus casei* var. *rhamnosus* NRRL-B-15972 has on mold growth when grown on cucumber agar was determined.

The procedure was as follows:

(1) Sterile tempered 10% (w/v) Noble agar was added to sterile filtered cuke juice 5% NaCl (w/v) to produce about 80% (v/v) cuke agar.

(2) The plate was spread with approximately 100 colonies of LCR on plates and incubated at 35° C. for 72 hours. The colonies were not visible until after 36 hours and had a good size at 72 hours.

(3) The cuke agar was overlayed with 0.75% (w/v) cuke agar with the following mold: (1) *Penicillium oxalicum*, (2) *Chaetomium olivacium*, (3) *Aspergillus terreus*, (4) *Verticillium sp*. It was found that after 72 hours there was no inhibition of *P. oxalicum*. There was retardation of growth of *Aspergillus terreus* and *Verticillium sp* and where *Lactobacillus casei* var. *rhamnosus* NRRL-B-15972 colonies were concentrated in one region of plate, there was a total inhibition. There was total inhibition of *Chaetomium olivacium*. After 5 days, the results were the same. Conodial development was stopped in *Aspergillus terreus*.

This experiment showed that *Lactobacillus casei* var. *rhamnosus* NRRL-B-15972 does inhibit some molds in a cucumber medium. It did not inhibit *P. oxalicum* and only partially inhibited *Aspergillus* and *Verticillium*. *Chaetomium olivacium* was completely inhibited.

EXAMPLE III

*Lactobacillus casei* var. *rhamnosus* NRRL-B-15972 is a rapid grower and as a mold and yeast inhibitor is a useful organism for the pickle industry. Mold and yeast growth on the surface of fermenting cukes are particularly bothersome. This experiment evaluated the growth of LCR in cucumber juices at two temperatures. Its mold inhibiting properties were also evaluated. It was compared with a commercial lactic acid producing culture, *Pediococcus pentosaceus*, used for this purpose.

The procedure was to puree 10 cucumbers in a blender. The puree was centrifuged and poured through cheese cloth under a vacuum. Chlorophyl was removed by centrifugation. NaCl was added to 5% concentration. The yield was 1660 mL of cucumber juice. The juice was filter sterilized through a 0.45 micron filter for immediate use. The remaining juice was frozen until ready for use.

The juice had a pH of 5.60 and contained 0.28% L-malic acid. LCR was added to 10 ml of pure juice and 60% juice to give $1 \times 10^6$ CFU/mL. The same procedure was used with *Pediocccus pentosaceus* NRRL-B-11,465. The unprocessed juice was incubated at 25° C. and at 15° C. The cuke juice contained 6 mL cuke juice; 0.5 mL of a 1:100 dil. *Lactobacillus casei* var. *rhamnosus* NRRL-B15972 or *Pediococcus pentosaceus* NRRL-B-11,465; 0.34 ml 5M NaCl; and 3.61 mL dH$_2$O (distilled water).

TABLE II

| | LCR* (100% juice) | LCR* (60% juice) | Pediococcus pentosaceus NRRL-B-11,465 | |
|---|---|---|---|---|
| | | | (100% juice) | (60% juice) |
| growth at 25° C. | + + | + + | + | + |
| growth at 18° C. | + | + | ± | ± |
| pH 65 hours 25° C. | 3.86 | 3.78 | 4.37 | 4.32 |
| pH 65 hours 18° C. | 4.97 | 4.40 | 5.65 | 5.54 |
| pH 90 hours 25° C. | 3.75 | 3.71 | 4.15 | 3.95 |
| pH 90 hours 18° C. | 4.23 | 4.01 | 5.27 | 4.64 |

*Lactobacillus casei var. rhamnosus NRRL-B-15972

Table II shows *Lactobacillus casei* var. *rhamnosus* NRRL-B-15972 is a very rapid fermenter and achieved lower pH's than *Pediococcus pentosaceus* NRRL-B-11,465.

In order to evaluate mold inhibition after 90 hours growth, 1 drop of a *P. oxalicum* spore suspension was added to each tube. A control tube of 100% cuke juice was adjusted to pH 3.77 with 85% lactic acid before the spores were added. The tubes were at 10° C. for 14 days. The results are shown in Table III

TABLE III

| Mold growth | | | | | |
|---|---|---|---|---|---|
| 60% PP* | 25° C. + + + + | 15° C. + + | Control + + + | | |
| 60% LCR** | 25° C. + | 15° C. + ± | | | |
| 100% PP | 25° C. + | 15° C. + + + + | | | |

TABLE III-continued

| 100% LCR | 25° C. ± | 15° C. +± |
|---|---|---|

+ = some growth
+++ = rapid growth
* = *Pediococcus pentosaceus*
** = *Lactobacillus casei* var. *rhamnosus* NRRL-B-15972

*Lactobacillus casei* var. *rhamnosus* NRRL-B-15972 grew more rapidly and lowered the pH faster than *Pediococcus pentosaceus* NRRL-B-11,465 in 100% and 60% juice at 25° and 18° C. Also *Lactobacillus casei* var. *rhamnosus*NRRL-B-15972 appeared to be more effective in inhibiting this mold even though it was not effective in Example II against the same fungi.

EXAMPLE IV

Procedure

Whole plant corn (variety: Dekalb XL 395A) at the early dent stage of maturity was cut by hand 5.0 cm above ground level. Plants were passed through a flail chopper and shredded into approximately 2.5 cm lengths (82.0 kg as-is; 25.0% dry matter). The plant material was mixed thoroughly and separated into three equal portions.

The three treatments utilized in this study were: (1) control - no additive, (2) *Pediococcus pentosaeus* NRRL-B-ll,465 additive 1, and (3) *Lactobacillus casei* var. *rhamnosus* NRRL-B-15972 additive 2. Plant material was inoculated at the rate of 100,000 bacteria per gram as-is forage, and $2.46 \times 10^7$ bacteria per gram as-is forage for additives 1 and 2 respectively.

Plant material for the control treatment was placed into a ribbon mixer and allowed to mix for approximately 10 minutes. The material was removed from the mixer, divided into 1,000 g portions, placed into plastic bags, compressed to remove as much air as possible, and sealed tightly. Twenty-four experimental silos were prepared so that 4 replicates could be opened after 0, 2, 3, 4, 8, and 28 days of treatment. Plant material for the microbial additive treatments was handled in the same way, except 67.0 ml of liquid containing the proper quantity of bacteria to inoculate the forage at the above rate was sprayed into the plant material as it mixed.

Day 0 silos were stored at −10° C. immediately after being prepared until analysis could be performed. Two days before analysis, these silos were removed from frozen storage and placed at 4.4° C to allow the material time to thaw. At the appropriate time, silos were opened, and material in the top 5.0 cm was discarded. A 400 g sample was placed into a forced air oven at 50 C for 48 hours for dry matter determination. The resulting dry sample was ground through a 1.0 mm screen and saved for chemical analysis. A 100 g sample was obtained from the middle of the silo and blended for 2 minutes with 400 ml distilled water. The resulting slurry was filtered through 8 layers of cheesecloth, and the filtrate saved. Filtrate pH was determined immediately, and 10.0 ml was added to a container containing 2.0 ml of 25% (w/v) meta-phosphoric acid and frozen until volatile fatty acid (VFA) analysis could be performed. Lactic and acetic acid contents were determined on the filtrate utilizing gas chromotography.

Laboratory dry matter and ash contents were determined by drying at 100° C for 24 hours, and igniting in a muffle furnace at 400° C for 5 hours. Neutral detergent fiber (NDF) and acid detergent fiber (ADF) contents of day 0 and 28 samples were determined according to the procedures of Goering and Van Soest (Goering, H. K. and P. J. Van Soest. 1970. Forage fiber analysis (Apparatus, Reagents, Procedure, and some applications. USDA Publication 387–398). In vitro organic matter digestibility (IVOMD) of day 0 and 28 samples was determined by a modification of a prior art technique (Tilley, J. M. A. and R. A. Terry. 1963. A two-stage technique for the in vitro digestion of forage crops. J. Brit. Grassl. Soc. 18:104 (1963)). Total crude protein content of day 0 and 28 samples was determined by the Kjeldahl technique (AOAC; Official methods of analysis of the association of official analytical chemists, 12th Edition. 1975). Acid detergent insoluble crude protein (ADICP) content of day 0 and 28 samples was determined as the total crude protein content of the residue remaining after the sample had been refluxed with ADF solution for 1.0 hour (Goering and Van Soest 1970).

Results

For all treatments, corn silage pH values declined, while lactic and acetic acid contents increased in a quadratic ($P<0.001$) manner over time. Immediately after being prepared, day 0 silos were stored at -10 C until chemical analysis could be performed. Two days before analysis, these silos were removed from the freezer and placed into a refrigerator at 4.4 C, and allowed to thaw. Fermentation occurred in these silos during this process, resulting in variable pH values for day 0 (Table IV).

TABLE IV

Effect of microbial additives on the pH of corn silage during the fermentation period.

| Treatment | day | | | | | |
|---|---|---|---|---|---|---|
| | 0 | 2 | 3 | 6 | 8 | 28 |
| Control | 5.26 | 4.22 | 4.01 | 3.71 | 3.69 | 3.64 |
| Additive 1 | 5.45 | 4.04 | 3.83 | 3.65 | 3.63 | 3.63 |
| Additive 2 | 5.27 | 3.88 | 3.72 | 3.55 | 3.55 | 3.56 |
| | P | | | | | |
| C vs A1[a] | .0001 | .0001 | .0001 | .008 | .0007 | .67 |
| C vs A2[a] | .62 | .0001 | .0001 | .0001 | .001 | .001 |

[a]C - control; A1 = Additive 1; A2 = Additive 2.

$a_C$- control; A1=Additive 1; A2=Additive 2. Inoculating whole plant corn with the microbial additives resulted in a more rapid decline in Ph relative to the control. By day 2, pH of corn silage that had been treated with the microbial additives was lower than that for the control This difference maintained itself throughout the fermentation period for additive 2, and from day 2 through 8 for additive 1. On day 28 there was no difference in corn silage pH between the control and additive 1.

Treating whole plant corn with the microbial additives resulted in a more rapid increase in lactic acid content relative to the control (Table V).

TABLE V

Effect of microbial additives on the lactic acid content of corn silage during the fermentation period.[a]

| Treatment | day | | | | | |
|---|---|---|---|---|---|---|
| | 0 | 2 | 3 | 6 | 8 | 28 |
| Control | 0 | 1.92 | 2.24 | 4.92 | 4.61 | 5.34 |
| Additive 1 | 0 | 4.16 | 4.78 | 6.26 | 5.16 | 5.84 |
| Additive 2 | 0 | 5.72 | 5.85 | 7.19 | 7.05 | 7.05 |
| | P | | | | | |
| C vs A1[b] | | .0001 | .0001 | .0005 | .20 | .28 |

TABLE V-continued

Effect of microbial additives on the lactic acid content of corn silage during the fermentation period.[a]

| Treatment | day 0 | 2 | 3 | 6 | 8 | 28 |
|---|---|---|---|---|---|---|
| C vs A2[b] | | .0001 | .0001 | .0001 | .0002 | .004 |

[a]Dry matter basis.
[b]C - control; A1 - additive 1; A2 - additive 2.

By day 2, lactic acid content of the inoculated silage was greater than that of the control. This difference maintained itself through the fermentation period for additive 2, and from day 2 through 6 for additive 1. By day 8, there was no difference in lactic acid content between the control and additive 1. Additive 2 produced significantly more lactic acid indicating that it was more competitive in the silage possibly because of its antifungal properties.

Inoculating whole plant corn with additive 1 resulted in greater acetic acid levels early in the fermentation period relative to the control. For additive 1, acetic acid levels were similar to the control following day 2, except on day 8 where levels were lower than the control. For additive 2, following day 2 acetic acid levels were lower than for the control. (Does this indicate that acetic acid is involved in antimicrobial activity?). The reslts are shown in Table VI.

TABLE VI

Effect of microbial additives on the acetic acid content of corn silage during the fermentation period.[a]

| Treatment | day 0 | 2 | 3 | 6 | 8 | 28 |
|---|---|---|---|---|---|---|
| Control | 0 | 0 | .46 | .90 | .98 | 1.36 |
| Additive 1 | 0 | .51 | .57 | .92 | .78 | 1.10 |
| Additive 2 | 0 | .22 | .30 | .36 | .43 | .61 |
| | | | | P | | |
| C vs A1[b] | | .0001 | .49 | .89 | .03 | .14 |
| C vs A2[b] | | .0002 | .33 | .004 | .0001 | .001 |

[a]Dry matter basis.
[b]C - Control; A1 - Additive 1; A2 - Additive 2.

Treating whole plant corn with the two microbial additives resulted in less dry matter loss at the end of the fermentation period, compared to the control (Table VII). No loss of dry matter was measured in experimental silos inoculated with microbial additive 1, and this was significantly less (P—0.004) than the 8,61% loss measured for the control. Dry matter loss of less than 1% for additive 2 was also less (P—0.007) than that for the control.

TABLE VII

Dry matter loss (%) of corn silage treated with microbial additives.

| | Treatment | | |
|---|---|---|---|
| Day | Control | Additive 1 | Additive 2 |
| 28 | 8.61 | 0.0 | 0.81 |

Fiber content, including NDF, ADF and hemicellulose, was not influenced by treating whole plant corn with the two microbial additives (Table VIII). On day 28, there was no difference in cell wall content (NDF) between the control and additive 1 (P—0.91), or between the control and additive 2 (P—0.49) Also, on day 28, there was no difference in ADF content between the control and additive 1 (OP—0.037) between the control and additive 2 (OP—0.31). The bacteria utilized to inoculate the plant material did not solubilize any hemicellulose to be utilized in their own metabolism. On day 28, there was no difference in corn silage hemicellulose content between the control and additive 1 (P—0.19) or between the control and additive 2 (P—0.78).

TABLE VIII

Fiber content (%) of corn silage treated with microbial additives.

| | NDF[a] | | | ADF[a] | | | HEMI[ab] | | |
|---|---|---|---|---|---|---|---|---|---|
| Day | C[c] | A-1 | A-2 | C | A-1 | A-2 | C | A-1 | A-2 |
| 0 | 57.32 | 48.01 | 57.42 | 29.11 | 32.23 | 35.02 | 28.20 | 25.78 | 22.40 |
| 28 | 58.11 | 58.33 | 59.55 | 32.52 | 34.04 | 34.23 | 25.59 | 24.29 | 25.32 |

[a]Ash free, organic matter basis.
[b]HEMI = hemicellulose = NDF - ADF
[c]C = Control, A-1 = Additive 1, A-2 = Additive 2.

In vitro organic matter digestibility (IVOMD) of the corn silage was not influenced by microbial treatment (Table IX). On day 28, there was no difference in corn silage IVOMD between the control and additive 1(OP—0.27) or between the control and additive 2(OP—(0.46)

TABLE IX

In vitro organic matter digestibility of corn silage treated with two microbial additives.

| | Treatment | | |
|---|---|---|---|
| Day | Control | Additive 1 | Additive 2 |
| 0 | 75.96 | 73.62 | 74.19 |
| 28 | 74.92 | 73.87 | 75.43 |

Crude protein (CP) content of corn plant material was increased by mirobial treatment. On day 28, CP content of silage was increased by treatment with additive 1 (OP—0.02) and additive 2 (P—0.0001) relative to the control The CP was significantly increased by additive 2. (Does this indicate protein generation or high cell counts? This would be significant). The results are shown in Table X.

TABLE X

Crude protein content (%) of corn silage treated with two microbial additives.[a]

| | Treatment | | |
|---|---|---|---|
| Day | Control | Additive 1 | Additive 2 |
| 0 | 6.55 | 8.16 | 7.89 |
| 28 | 6.68 | 7.75 | 9.20 |

[a]Dry matter basis.

Acid detergent insoluble crude protein (ADICP) content represents the quantity of protein that is unavailable to the ruminant animal. Feedstuffs that undergo heat treatment during processing have increased ADICP content relative to those that experience no heat treatment. The ADICP procedure provides an estimate of heat damage that occurs during the fermentation process. Corn silage ADICP content was no influenced by microbial treatment (C vs Al:P=0.30; C vs A2:P=0.43). The results are shown in Table XI.

TABLE XI

Acid detergent insoluble crude protein content (%) of corn silage treated with two microbial additives.[a]

| | Treatment | | |
|---|---|---|---|
| Day | Control | Additive 1 | Additive 2 |
| 0 | .44 | .52 | .62 |

TABLE XI-continued

Acid detergent insoluble crude protein content (%) of corn silage treated with two microbial additives.[a]

| Day | Treatment | | |
|---|---|---|---|
| | Control | Additive 1 | Additive 2 |
| 28 | .47 | .57 | .55 |

[a] Dry matter basis.

No mold was evident in any of the control or additive 1 or additive 2 experiments; since the silage did not contain fungi. Had fungi been added they would have been inhibited to a certain degree although the effect is not as pronounced as on agar as in Example II.

It will be appreciated that the *Lactobacillus casei* var. *rhamnosus* NRRL-B-15972 can be used in a variety of ways for its antifungal properties. All of these variations of the present invention will be obvious to those skilled in the art as a result of the present disclosure.

What is claimed is:

1. A method of treating a material to inhibit fungal growth which comprises incorporating in or on the material living cells of *Lactobacillus casei* var. *rhamnosus* NRRL-B-15972 which produces an antifungal substance and inhibits the fungal growth.

2. The method of claim 1 wherein the material is a food and wherein the cells are maintained as living cells in the food.

3. The method of claim 2 wherein the food is fermented by the Lactobacillus.

4. The method of claim 2 wherein at least about $10^5$ cells per ml are introduced into the food.

5. The method of claim 2 wherein between about $10^6$ and $10^8$ cells per gram of material are incorporated.

* * * * *

UNITED STATES PATENT AND TRADEMARK OFFICE
CERTIFICATE OF CORRECTION

PATENT NO. : 4,956,177

DATED : September 11, 1990

INVENTOR(S) : Stephen W. King, et al

It is certified that error appears in the above-identified patent and that said Letters Patent is hereby corrected as shown below:

Column 2, line 13, "NRRL-B-19572" should be
--NRRL-B-15972--.

Column 2, line 65, "NRRL-B-19572" should be
--NRRL-B-15972--.

Column 3, line 1, "NRRL-B-19572" should be
--NRRL-B-15972--.

Column 3, line 2, "studies" should be --studied--.

Column 3, line 21, after "each", --additive and-- should be inserted.

Column 3, line 27, "culture - 2.5" should be
--culture = 2.5--.

Column 4, line 29, "Pediocccus" should be --Pediococcus--.

Column 4, line 34, "3.61 mL" should be --3.16 mL--.

UNITED STATES PATENT AND TRADEMARK OFFICE
CERTIFICATE OF CORRECTION

PATENT NO. : 4,956,177

DATED : September 11, 1990

INVENTOR(S) : Stephen W. King, et al

It is certified that error appears in the above-identified patent and that said Letters Patent is hereby corrected as shown below:

Column 5, line 50, "50 C" should be --50°C--.

Column 5, line 62, "chromotography" should be --chromatography--.

Column 6, line 24, "-10 C" should be -- -10°C --.

Column 6, line 27, "4.4 C" should be -- 4.4°C --.

Column 6, line 45, "aC-control; A1=Additive 1; A2=Additive 2." should be deleted.

Column 6, line 49, a period --.-- should be inserted after "control".

Column 7, line 28, "rslts" should be --results--.

Column 7, line 48, "8,61%" should be --8.61%--.

Column 7, line 67, "(OP-0.037)" should be --(P-0.37)--.

Column 7, line 68, "(OP-0.31)" should be --(P-0.31)--.

Column 8, line 9, after "with", --two-- should be inserted.

Column 8, line 23, "(OP-0.27)" should be --(P-0.27)--.

UNITED STATES PATENT AND TRADEMARK OFFICE
CERTIFICATE OF CORRECTION

PATENT NO. : 4,956,177

DATED : September 11, 1990

INVENTOR(S) : Stephen W. King, et al

It is certified that error appears in the above-identified patent and that said Letters Patent is hereby corrected as shown below:

Column 8, line 24, "(OP-(0.46)" should be --(P-0.46)--.

Column 8, line 34, "mirobial" should be --microbial--.

Column 8, line 38, a period --.-- should be inserted after "control".

Column 8, line 58, "no" should be --not--.

Signed and Sealed this

Seventeenth Day of November, 1992

*Attest:*

DOUGLAS B. COMER

*Attesting Officer*     Acting Commissioner of Patents and Trademarks